(12) United States Patent
Konieczny et al.

(10) Patent No.: US 7,638,477 B2
(45) Date of Patent: Dec. 29, 2009

(54) SUSTAINED-RELEASE FRAGRANCE DELIVERY SYSTEM

(75) Inventors: Michael F. Konieczny, Palatine, IL (US); Larry Alania, Naperville, IL (US); Varsha K. Shah, Streamwood, IL (US); Shannon Lea McKenzie, Chicago, IL (US)

(73) Assignee: Alberto-Culver Company, Melrose Park, IL (US)

( * ) Notice: Subject to any disclaimer, the term of this patent is extended or adjusted under 35 U.S.C. 154(b) by 235 days.

(21) Appl. No.: 11/076,348

(22) Filed: Mar. 9, 2005

(65) Prior Publication Data

US 2006/0205616 A1 Sep. 14, 2006

(51) Int. Cl.
C11D 3/37 (2006.01)
(52) U.S. Cl. .................. 510/470; 512/4; 516/1
(58) Field of Classification Search ............ 510/470; 512/4; 516/1
See application file for complete search history.

(56) References Cited

U.S. PATENT DOCUMENTS

| | | | |
|---|---|---|---|
| 3,314,803 A | 4/1967 | Dame, Jr. et al. |
| 3,373,126 A | 3/1968 | Lehrman et al. |
| 3,455,838 A | 7/1969 | Marotta et al. |
| 3,846,404 A | 11/1974 | Nichols |
| 3,939,099 A | 2/1976 | Tusa et al. |
| 3,971,852 A | 7/1976 | Brenner et al. |
| 3,985,298 A | 10/1976 | Nichols |
| 4,029,726 A | 6/1977 | Nichols |
| 4,080,439 A | 3/1978 | Pomot et al. |
| 4,122,192 A | 10/1978 | Fellows |
| 4,161,449 A | 7/1979 | Smith et al. |
| 4,243,548 A | 1/1981 | Heeb et al. |
| 4,386,112 A | 5/1983 | Eaton et al. |
| 4,450,151 A | 5/1984 | Shinozawa |
| 4,532,145 A | 7/1985 | Saleeb et al. |
| 4,566,980 A | 1/1986 | Smith |
| 4,678,598 A | 7/1987 | Ogino et al. |
| 4,690,825 A | 9/1987 | Won |
| 4,756,759 A | 7/1988 | Amon et al. |
| 4,906,488 A | 3/1990 | Pera |
| 4,946,870 A | 8/1990 | Partain, III. et al. |
| 4,961,532 A | 10/1990 | Tangney |
| 5,013,557 A | 5/1991 | Tai |
| 5,073,365 A | 12/1991 | Katz et al. |

(Continued)

FOREIGN PATENT DOCUMENTS

EP 0 285 722 B1 10/1988

(Continued)

*Primary Examiner*—John R Hardee
(74) *Attorney, Agent, or Firm*—Leydig, Voit & Mayer, Ltd.

(57) ABSTRACT

The invention provides a method of producing a personal care product comprising combining a fragrance, a propellant and porous carrier particles, to produce a composition substantially free of pre-encapsulated fragrance particles, and containing the composition in a pressurized container. Also provided is a personal care product comprising a pressurized container and a composition contained therein, which includes a fragrance, a propellant and porous carrier particles, wherein the composition is substantially free pre-encapsulated fragrance particles. When the composition is released from the container, the propellant evaporates rapidly to produce a matrix, which incorporates the fragrance into the pores of the carrier, to produce a sustained-release fragrance delivery system.

23 Claims, 1 Drawing Sheet

U.S. PATENT DOCUMENTS

| | | | |
|---|---|---|---|
| 5,135,747 A | 8/1992 | Faryniarz et al. | |
| 5,156,833 A | 10/1992 | Osugi et al. | |
| 5,159,472 A | 10/1992 | Miyabayashi | |
| 5,176,903 A | 1/1993 | Goldberg et al. | |
| 5,194,262 A | 3/1993 | Goldberg et al. | |
| 5,206,019 A | 4/1993 | Nichols | |
| 5,223,251 A | 6/1993 | Nichols | |
| 5,223,260 A | 6/1993 | Morgan et al. | |
| 5,228,150 A | 7/1993 | Parker | |
| 5,238,915 A | 8/1993 | Fuwa et al. | |
| 5,254,295 A | 10/1993 | Grassi et al. | |
| 5,290,570 A | 3/1994 | Nichols | |
| 5,318,778 A * | 6/1994 | Schmucker et al. | 424/401 |
| 5,322,696 A | 6/1994 | Morgan et al. | |
| 5,336,665 A | 8/1994 | Garner-Gray et al. | |
| 5,362,425 A | 11/1994 | Schrier | |
| 5,426,163 A | 6/1995 | Buehler et al. | |
| 5,429,628 A | 7/1995 | Trinh et al. | |
| 5,436,437 A | 7/1995 | Ho | |
| 5,455,049 A | 10/1995 | Anaebonam et al. | |
| 5,476,519 A | 12/1995 | Haslop et al. | |
| 5,482,927 A | 1/1996 | Maniar et al. | |
| 5,506,353 A | 4/1996 | Subramaniam | |
| 5,525,367 A | 6/1996 | King et al. | |
| 5,540,853 A | 7/1996 | Trinh et al. | |
| 5,585,093 A | 12/1996 | Murphy | |
| 5,587,170 A | 12/1996 | Caisey et al. | |
| 5,599,555 A | 2/1997 | El-Nokaly | |
| 5,605,682 A * | 2/1997 | Ross et al. | 424/68 |
| 5,667,806 A | 9/1997 | Kantor | |
| 5,679,324 A | 10/1997 | Lisboa et al. | |
| 5,691,303 A | 11/1997 | Pan et al. | |
| 5,714,445 A | 2/1998 | Trinh et al. | |
| 5,766,690 A | 6/1998 | Derby et al. | |
| 5,776,856 A | 7/1998 | Narayanan | |
| 5,794,859 A | 8/1998 | Goenka et al. | |
| 5,800,805 A | 9/1998 | Salas | |
| 5,837,327 A | 11/1998 | Sue et al. | |
| 5,843,881 A | 12/1998 | Dubois et al. | |
| 5,861,143 A | 1/1999 | Peterson et al. | |
| 5,861,144 A | 1/1999 | Peterson et al. | |
| 5,871,722 A | 2/1999 | Nacht et al. | |
| 5,876,755 A | 3/1999 | Perring et al. | |
| 5,919,486 A | 7/1999 | Ishii et al. | |
| 5,919,752 A | 7/1999 | Morelli et al. | |
| 5,928,194 A | 7/1999 | Maget | |
| 5,945,085 A | 8/1999 | Salas et al. | |
| 5,980,604 A | 11/1999 | Lavernia | |
| 5,993,805 A | 11/1999 | Sutton et al. | |
| 6,013,618 A | 1/2000 | Morelli et al. | |
| 6,020,003 A | 2/2000 | Stroh et al. | |
| 6,042,792 A | 3/2000 | Shefer et al. | |
| 6,045,823 A | 4/2000 | Vollhardt et al. | |
| 6,071,324 A | 6/2000 | Laul et al. | |
| 6,083,456 A | 7/2000 | Van Rees | |
| 6,086,903 A | 7/2000 | Trinh et al. | |
| 6,132,744 A | 10/2000 | Chehab et al. | |
| 6,143,324 A | 11/2000 | Michaud et al. | |
| 6,156,826 A | 12/2000 | Guénin et al. | |
| 6,190,591 B1 | 2/2001 | van Lengerich | |
| 6,200,949 B1 | 3/2001 | Reijmer et al. | |
| 6,221,399 B1 | 4/2001 | Rolfes et al. | |
| 6,224,939 B1 | 5/2001 | Cherukuri et al. | |
| 6,248,338 B1 | 6/2001 | Müller et al. | |
| 6,254,704 B1 | 7/2001 | Laul et al. | |
| 6,254,823 B1 | 7/2001 | Rees | |
| 6,258,857 B1 | 7/2001 | Iijima et al. | |
| 6,344,183 B2 | 2/2002 | Paul et al. | |
| 6,365,189 B1 | 4/2002 | Quong | |
| 6,395,290 B2 | 5/2002 | Brown | |
| 6,406,684 B1 | 6/2002 | Fecht et al. | |
| 6,432,415 B1 | 8/2002 | Osborne et al. | |
| 6,482,433 B1 | 11/2002 | De Roos et al. | |
| 6,485,707 B2 | 11/2002 | Zhu et al. | |
| 6,531,444 B1 | 3/2003 | Shefer et al. | |
| 6,537,813 B1 | 3/2003 | Chen et al. | |
| 6,544,497 B2 | 4/2003 | Zhu et al. | |
| 6,551,578 B2 | 4/2003 | Adjei et al. | |
| 6,596,262 B2 | 7/2003 | Zhu et al. | |
| 2001/0038879 A1 | 11/2001 | Mutka et al. | |
| 2002/0016269 A1 | 2/2002 | Noda et al. | |
| 2002/0119117 A1 | 8/2002 | Zhu et al. | |
| 2003/0024997 A1 | 2/2003 | Welch et al. | |
| 2003/0036489 A1 | 2/2003 | Liu et al. | |
| 2003/0044440 A1 | 3/2003 | Toumi | |
| 2003/0069165 A1 | 4/2003 | Malton et al. | |
| 2003/0119713 A1 | 6/2003 | Heltovics et al. | |
| 2003/0211125 A1 | 11/2003 | Heltovics et al. | |
| 2004/0001891 A1 | 1/2004 | Smith et al. | |
| 2004/0081627 A1 | 4/2004 | Jinks et al. | |
| 2005/0238597 A1 * | 10/2005 | McCook et al. | 424/66 |

FOREIGN PATENT DOCUMENTS

| | | |
|---|---|---|
| EP | 0 570 085 A2 | 11/1993 |
| EP | 0 674 899 A2 | 10/1995 |
| EP | 0 684 038 A2 | 11/1995 |
| EP | 0 550 067 B1 | 9/1996 |
| EP | 0 480 520 B2 | 10/1999 |
| EP | 0 965 326 A1 | 12/1999 |
| EP | 0 684 984 B2 | 2/2001 |
| EP | 1 203 578 A1 | 5/2002 |
| EP | 1 443 058 A1 | 8/2004 |
| JP | 55085515 A | 6/1980 |
| JP | 60047090 A | 3/1985 |
| WO | WO 98/16205 A2 | 4/1998 |
| WO | WO 01/07710 A1 | 2/2001 |
| WO | WO 01/85136 A2 | 11/2001 |
| WO | WO 01/97768 A2 | 12/2001 |
| WO | WO 02/34226 A1 | 5/2002 |
| WO | WO 02/089862 A2 | 11/2002 |

* cited by examiner

SUSTAINED-RELEASE FRAGRANCE DELIVERY SYSTEM

FIELD OF THE INVENTION

This invention pertains to sustained-released fragrance delivery systems, methods of producing sustained-released fragrance delivery systems, and associated products.

BACKGROUND OF THE INVENTION

Personal care compositions for sustained released fragrance delivery are known in the art. Conventional sustained release fragrance delivery systems typically utilize particles containing a pre-encapsulated fragrance to provide for sustained-released delivery of the fragrance. Conventional pre-encapsulated fragrance particles are produced by combining carrier particles (typically starch) and a fragrance in an aqueous medium and spray-drying the mixture at high temperatures (e.g., from about 132° C. to about 204° C.).

The conventional spray drying technique is believed to be necessary for incorporating the fragrance into the carrier material sufficiently to promote gradual release of the fragrance over time. The resulting spray-dried product is then combined with a propellant and other ingredients, and stored in a pressurized container with a release valve (e.g., a spray nozzle) allowing the end user to deliver the composition as an aerosol.

While the conventional pre-encapsulation process is thought to adequately provide a time-released fragrance delivery system, there are disadvantages. For instance, the spray-drying process is not only expensive, but also requires the use of water and high temperatures. The aqueous spray drying process may degrade or reduce the effectiveness of fragrance compositions that are sensitive to such conditions, e.g., fragrances with one or more components that are volatile, thermally sensitive, or unstable in a hot aqueous environment. Fragrances derived from natural sources, e.g., plant extracts, are especially vulnerable. In this regard, the conventional pre-encapsulation process can degrade or eliminate one or more desirable fragrance "notes" that otherwise would have been present in the underlying fragrance.

Conventional pre-encapsulated fragrance products also have inherent problems associated with clogging, making it difficult to consistently and reliably deliver the product as an aerosol. Accordingly, there is a need for a sustained release fragrance delivery product and a method of producing a sustained release fragrance delivery product that overcomes the disadvantages associated with conventional pre-encapsulated fragrance systems.

The invention provides such a product and method. These and other advantages of the invention, as well as additional inventive features, will be apparent from the description of the invention provided herein.

BRIEF SUMMARY OF THE INVENTION

The present invention provides a method of producing a personal care product, which includes combining a fragrance, a propellant and porous carrier particles, to produce a composition, which is substantially free of pre-encapsulated fragrance particles, and containing the composition within a pressurized container. The present invention also provides a personal care product comprising a pressurized container and a composition contained therein, wherein the composition includes a fragrance, a propellant and a carrier, which is substantially free of pre-encapsulated fragrance particles.

The invention further provides a method of producing a fragrance delivery system comprising expelling from a pressurized container a composition comprising a fragrance, a propellant and a carrier, wherein the composition is substantially free of pre-encapsulated fragrance particles. When the composition is expelled from the container, the propellant evaporates rapidly to produce a matrix, which incorporates the fragrance into the pores of the carrier particles and releases the fragrance gradually over time.

The carrier used in accordance with the present invention consists essentially of porous carrier particles, at least about 95% of which have diameters of less than about 70 μm.

DETAILED DESCRIPTION OF THE INVENTION

Figure 1:
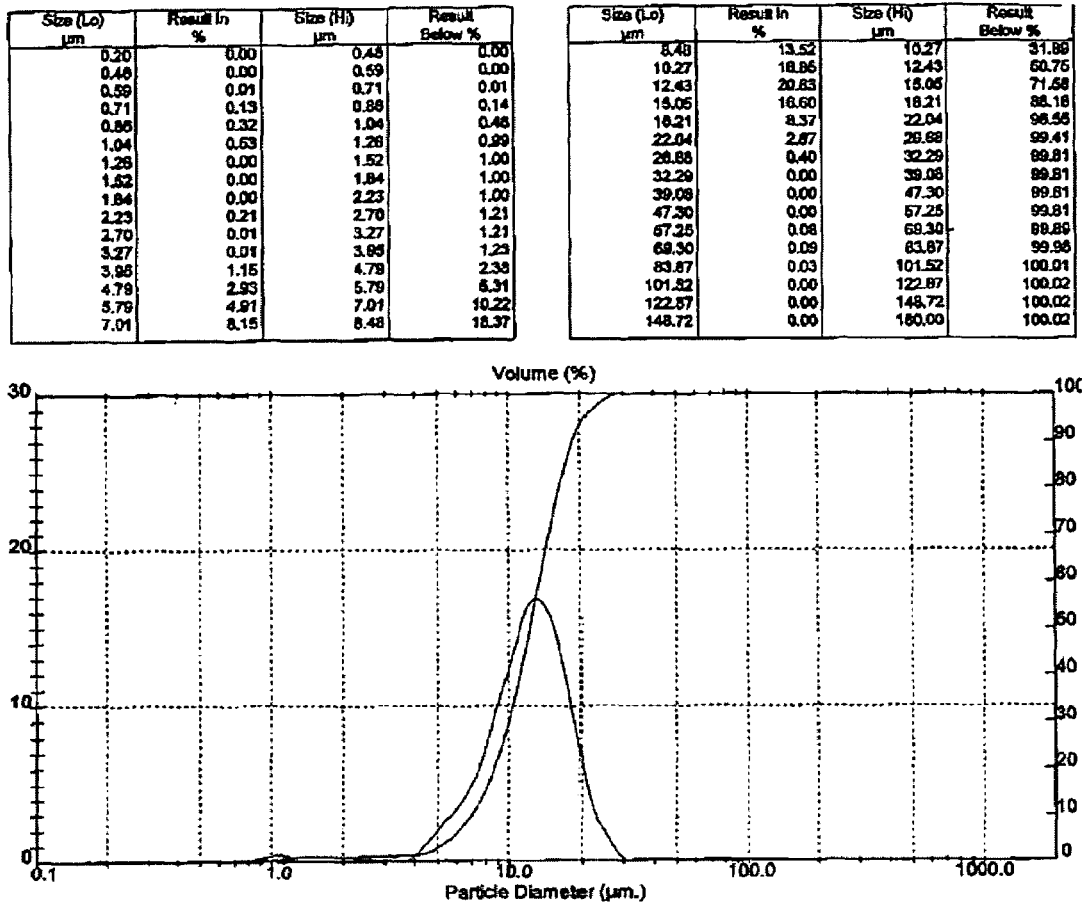
FIG. 1 depicts particle size distribution data for an exemplary carrier used in accordance with the present invention.

The present invention provides a method of producing a personal care product, which includes combining a fragrance, a propellant and carrier particles to produce a composition, which is substantially free of pre-encapsulated fragrance particles. The composition is contained within a pressurized container, which preferably provides for delivery of the composition, e.g., as an aerosol.

The present invention further provides a method of producing a fragrance delivery system, which includes expelling from a pressurized container a composition that includes a fragrance, a propellant, and carrier particles, wherein the composition is substantially free of pre-encapsulated fragrance particles. When the composition is expelled from the container, the propellant evaporates rapidly (e.g., within a few seconds or less at atmospheric pressure) to produce a matrix, which incorporates the fragrance into the pores of the carrier particles, to produce a sustained-release delivery system, which releases the fragrance gradually over time.

The present invention additionally provides a personal care product comprising a pressurized container and a composition contained therein, which includes a fragrance, a propellant and carrier particles, wherein the composition is substantially free pre-encapsulated fragrance particles. The methods and products of the present invention avoid the use of pre-encapsulated fragrance particles, obviating the need for costly and harsh hot aqueous spray drying methods used for producing conventional sustained release fragrance delivery systems.

Moreover, the sustained release delivery system of the present invention exhibits improvements in product performance and quality over the conventional products, which use pre-encapsulated particles. For instance, the present invention provides for consistent and reliable delivery of a sustained release fragrance delivery system as an aerosol, using conventional pressurized aerosol containers, without clogging associated with conventional pre-encapsulated products. In addition, the sustained release delivery system of the present invention has improved tactile properties, e.g., noticeably improved smoothness in texture, relative to conventional products, which use pre-encapsulated particles.

The carrier used in the composition of the present invention preferably consists essentially of porous carrier particles, at least about 95% of which have diameters of less than about 70 μm. Preferably, at least about 95% (e.g., 95% or greater, 96% or greater, 97% or greater, 98% or greater, or 99% or greater) of the porous carrier particles have diameters of less than about 70 μm (microns) (e.g., 70 μm or less, 68 μm or less, 65

μm or less, 63 μm or less, 60 μm or less, 58 μm or less or 55 μm or less). More preferably, at least about 97% of the porous carrier particles have diameters of less than about 70 μm. Still more preferably, at least about 99% (e.g., at least about 99.9%) of the porous carrier particles have diameters of less than about 70 μm.

In is also preferred that at least about 80% (e.g., 80% or greater, 85% or greater, 87% or greater, 90% or greater, 93% or greater, 95% or greater, 97% or greater, or 99% or greater) of the porous carrier particles have diameters within about 10 μm of the median diameter of the particles (i.e., from about 10 μm greater than to about 10 μm less than the median diameter). The median diameter of the porous carrier particles is preferably from about 5 μm to about 60 μm. The median diameter of the porous carrier particles can range, e.g., from 5 μm to 60 μm, from about 5 μm to about 55 μm, from about 5 μm to about 50 μm, from about 5 μm to about 45 μm, from about 5 μm to about 40 μm, from about 5 μm to about 35 μm, from about 5 μm to about 30 μm, from about 5 μm to about 25 μm, or from about 5 μm to about 20 microns.

The median diameter of the porous carrier particles also can range, e.g., from about 10 μm to about 50 μm, from about 10 μm to about 45 μm, from about 10 μm to about 40 μm, from about 10 μm to about 35 μm, from about 10 μm to about 30 μm, from about 10 μm to about 25 μm, or from about 10 μm to about 20 μm. Alternatively, the median diameter of the porous carrier particles also can range, e.g., from about 15 μm to about 50 μm, from about 15 μm to about 45 μm, from about 15 μm to about 40 μm, from about 15 μm to about 35 μm, from about 15 μm to about 30 μm, from about 15 μm to about 25 μm, from about 15 μm to about 20 microns, from about 20 μm to about 50 μm, from about 20 μm to about 45 μm, from about 20 μm to about 40 μm, from about 20 μm to about 35 μm, from about 20 μm to about 30 μm, or from about 20 μm to about 25 μm. Particle size distribution data for an exemplary carrier used in accordance with the present invention is provided in FIG. 1.

The term "pre-encapsulated" as used herein refers to fragrance delivery systems, which utilize conventional fragrance-encapsulated particles produced by the aqueous spray drying process described above. As indicated above, the product of the present invention is substantially free of such pre-encapsulated fragrance particles.

While applicants do not wish to be bound by any particular theory, it is believed that conventional aqueous spray drying processes may cause porous carrier particles to undergo structural changes, particularly on the exterior and, possibly, interstitial surfaces thereof, causing the particles to "ripen" and/or agglomerate. The applicants have found that such carrier particles, surprisingly and unexpectedly, do not undergo any significant structural changes such as ripening or agglomeration when formulated in accordance with the present invention. Although applicants do not wish to be bound by any particular theory, it is believed that the improved properties exhibited by the product of the present invention may, at least in part, be attributable to improvements in properties of the carrier particles.

Any suitable fragrance can be used in accordance with the present invention. Suitable fragrances can include, e.g., synthetic fragrances, natural fragrances, and combinations thereof. Suitable fragrances can include, e.g., oils, plant extracts, and the like, and mixtures thereof. The fragrances can be soluble or insoluble in the propellant and can include a single fragrance compound or a blend of one or more fragrance compounds in accordance with the invention. The personal care product of the invention can comprise any suitable amount of fragrance. For example, the fragrance can be present in the personal care product in an amount of, e.g., from about 0.01% by weight to about 10% by weight, from about 0.01% by weight to about 5% by weight, from about 0.1% by weight to about 3% by weight, from about 0.1% by weight to about 2.5% by weight, or from about 0.1% by weight to about 1% by weight (e.g., about 0.5 wt %).

Any suitable propellant can be used in accordance with the present invention. Suitable propellants can include one or more liquefied compressed gases. Such propellants can include, for example, hydrocarbon propellants (e.g., isobutane or propane), fluorocarbon propellants (e.g., hydrofluorocarbon 152a), fluorochlorocarbon propellants, hydrochlorocarbon propellants, ether propellants (e.g., dimethyl ether), and the like, and mixtures thereof. The personal care product of the invention can comprise any suitable amount of propellant. For example, the propellant can be present in the personal care product in an amount of, e.g., from about 80% by weight to about 98% by weight, from about 80% by weight to about 95% by weight, from about 80% by weight to about 90% by weight, from about 85% by weight to about 90% by weight, from about 85% by weight to about 95% by weight, or from about 90% by weight to about 95% by weight.

The porous carrier particles can be manufactured from any suitable material, which is preferably capable of promoting binding of fragrance molecules to the surfaces and/or interstices of the carrier particles sufficiently to provide sustained release delivery. The porous carrier particles can include, for example, one or more polymers (e.g., natural polymers; synthetic polymers, such as, e.g., polymethacrylate, nylon, styrene, polystyrene, and the like, and mixtures thereof), one or more dextrins (e.g., cyclodextrin), and/or one or more inorganic materials (e.g., sodium bicarbonate, silica, fumed silica, colloidal silica, magnesium aluminum silicate, aluminum silicate, magnesium silicate, clay, and the like, and mixtures thereof).

Preferably the polymer includes one or more a polysaccharides, e.g., one or more polysaccharides selected from the group consisting of starches, celluloses, and the like, and combinations thereof. Suitable starches can include, e.g., corn starch, modified corn starch, tapioca starch, modified tapioca starch, potato starch, modified potato starch, wheat starch, modified wheat starch, and the like, and mixtures thereof. Suitable celluloses can include, for example, celluloses and derivatives thereof, e.g., ethyl cellulose, methyl cellulose, propylmethyl cellulose, hydroxyethyl cellulose, hydroxymethyl cellulose, hydroxypropylmethyl cellulose, and the like, and mixtures thereof. In a particularly preferred embodiment, the porous carrier particles are made from corn starch, tapioca starch or a combination thereof.

The personal care product of the invention can include any suitable amount of porous carrier particles. For example, the porous carrier particles can be present in the personal care product of the invention in an amount of, e.g., from about 1% by weight to about 20% by weight, from about 1% by weight to about 15% by weight, from about 1% by weight to about 10% by weight, from about 1% by weight to about 8% by weight, from about 1% by weight to about 5% by weight, or from about 2% by weight to about 5% by weight (e.g., about 3 wt %).

Any suitable container capable of containing the composition of the present invention under pressure can be used in accordance with the present invention. The pressurized container preferably includes at least one valve capable of expelling (e.g., for controllable release or delivery by an end user) at least a portion of the composition from the container. The valve opening can have any suitable diameter, and preferably is capable of expelling at least a portion of the composition from the pressurized container as an aerosol. In a particularly preferred embodiment, the pressurized container includes a valve, wherein the diameter of the opening of the valve is about 210 μm.

The following examples further illustrate the invention but, of course, should not be construed as in any way limiting its scope.

EXAMPLE 1

This example demonstrates the method for producing a personal care product of the present invention. The components of the composition in the product are listed in Table 1.

TABLE 1

| Ingredients | wt % |
|---|---|
| Fragrance Oil | 0.6 |
| Mineral Oil and Lanolin Alcohol and Oleyl Alcohol | 0.1 |
| Isopropyl Myristate | 4.5 |
| Benzyl Alcohol | 0.1 |
| Magnesium Stearate | 1.5 |
| Sodium Bicarbonate | 0.1 |
| Isobutane Propellant | 90.0 |
| Corn Starch | 3.1 |

Into a steel tank equipped with an Ystral™ Homomill and a Lightening™ mixer is added isopropyl myristate (4.5% of the composition by weight). With moderate agitation, the following ingredients are then added: benzyl alcohol (0.1% by weight), a mixture of mineral oil with lanolin alcohol and oleyl alcohol (0.1% by weight), and fragrance oil (0.6% by weight). The mixer agitation is then increased, and the mixture is recirculated through the Ystral™ Homomill. The following powder materials are then added in order slowly to avoid clumping: magnesium stearate (1.5% by weight), *zea mays* (corn) starch sold by National Starch and Chemical Co. as Purity 21C Pure (in which 99.89% of the particles have a diameter less than 69.30 μm, 3.1% by weight), and sodium bicarbonate (0.1% by weight). The particle size distribution data of the corn starch is provided in FIG. 1. Mixing and recirculating is performed for a minimum of 5 minutes.

After mixing is complete, the mixture is pumped into a run tank equipped with adequate mixing capabilities, and constant mixing is maintained throughout the filling operation. The mixture is passed through a Cuno™ Motorized Filter with a setting of 90 μm before filling. Pressurizeable containers are then filled with the concentrated mixture. After the containers are vacuum crimped, they are pressure filled with isobutane propellant (90.0% by weight).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of producing a personal care product, the method comprising combining a fragrance, a propellant and porous carrier particles, which consist essentially of unmodified starch, are free of pre-encapsulated fragrance and at least about 95% of which have a diameter of less than about 70 μm, and containing the composition within a pressurized container to produce the personal care product, wherein when the resulting composition is expelled from the container, the propellant evaporates rapidly and the resulting carrier particles release the fragrance gradually over time.

2. The method of claim 1, wherein at least about 97% of the carrier particles have a diameter of less than about 70 μm.

3. The method of claim 1, wherein at least about 80% of the carrier particles have a diameter within about 10 μm of the median diameter of the particles.

4. The method of claim 1, wherein at least about 90% of the carrier particles have a diameter within about 10 μm of the median diameter of the particles.

5. The method of claim 1, wherein at least about 95% of the carrier particles have a diameter within about 10 μm of the median diameter of the particles.

6. The method of claim 1, wherein the carrier particles have a median diameter of from about 5 μm to about 60 μm.

7. The method of claim 1, wherein the carrier particles have a median diameter of from about 10 μm to about 50 μm.

8. The method of claim 1, wherein the starch is selected from corn starch, tapioca starch, wheat starch, and mixtures thereof.

9. The method of claim 8, wherein the starch is a corn starch.

10. The method of claim 9, wherein at least about 90% of the carrier particles have a diameter within about 10 μm of the median diameter of the particles.

11. The method of claim 10, wherein the carrier particles have a median diameter of from about 10 μm to about 30 μm.

12. The method of claim 8, wherein the starch is a tapioca starch.

13. The method of claim 1, wherein the pressurized container comprises at least one valve capable of allowing at least a portion of the composition to be expelled from the container.

14. The method of claim 13, wherein the valve is capable of expelling the composition from the pressurized container as an aerosol.

15. The method of claim 1, wherein the propellant is a liquefied compressed gas.

16. The method of claim 1, wherein the propellant is selected from the group consisting of isobutene, propane, hydrofluorocarbon 152a, dimethyl ether, and mixtures thereof.

17. The method of claim 1, wherein at least a portion of the fragrance is dissolved in the composition.

18. A method of applying a fragrance delivery system, the method comprising expelling the composition prepared according to claim 1 from the pressurized container, wherein when the composition is expelled from the container, the propellant evaporates rapidly and the resulting carrier particles release the fragrance gradually over time.

19. The method of claim 1, wherein the resulting composition comprises from about 0.01 wt % to about 5 wt % fragrance, from about 80 wt % to about 95 wt % propellant and from about 1 wt % to about 10 wt % porous unmodified starch particles.

20. The method of claim 19, wherein the composition comprises from about 0.1 wt % to about 3 wt % fragrance, from about 85 wt % to about 95 wt % propellant and from about 1 wt % to about 5 wt % porous unmodified starch particles.

21. The method of claim 20, wherein the composition comprises from about 0.1 wt % to about 2.5 wt % fragrance and from about 2 wt % to about 5 wt % porous unmodified starch particles.

22. The method of claim 21, wherein the composition comprises from about 0.1 wt % to about 1 wt % fragrance.

23. The method of claim 1, wherein the composition contained within the pressurized container consists essentially of 0.6 wt % fragrance, 90 wt % propellant, 3.1 wt % corn starch 0.1 wt % of a combination of mineral oil, lanolin alcohol and oleyl alcohol, 4.5 wt % isopropyl myristate, 0.1 wt % benzyl alcohol, 1.5 wt % magnesium stearate, and 0.1 wt % sodium bicarbonate.

* * * * *